United States Patent [19]

Hansen et al.

[11] Patent Number: 5,955,277
[45] Date of Patent: Sep. 21, 1999

[54] MUTANT CDNA ENCODING THE P85α SUBUNIT OF PHOSPHATIDYLINOSITOL 3-KINASE

[75] Inventors: Torben Hansen, Hellerup, Denmark; Carsten Bo Andersen, Los Altos, Calif.; Oluf Borbye Pedersen, Holte, Denmark

[73] Assignee: Novo Nordisk A/S, Bagsvaerd, Denmark

[21] Appl. No.: 08/850,993

[22] Filed: May 5, 1997

[51] Int. Cl.[6] .............................. C12Q 1/68; C12P 19/34; C07H 21/02
[52] U.S. Cl. ............................. 435/6; 435/91.2; 536/23.1
[58] Field of Search ...................... 435/6, 91.2; 536/22.1, 536/23.1

[56] References Cited

U.S. PATENT DOCUMENTS 5,434,064  7/1995  Schlessinger et al. ................ 435/172.3

FOREIGN PATENT DOCUMENTS

WO 92/13001  8/1992  WIPO .
WO 96/12024  4/1996  WIPO .

OTHER PUBLICATIONS

Otsu et al, Cell 65: 91–104, 1991.
Skolnik et al, Cell 65: 83–90, 1991.
Hara et al., Proc. Nat'l. Acad. Sci., vol. 91, pp. 7415–7419 (1994).
Hansen, et al., Dialog accession No. 08999990.
Hansen, et al., Dialog accession No. 14981552.

*Primary Examiner*—Eggerton A. Campbell
*Attorney, Agent, or Firm*—Steve T. Zelson, Esq.; Reza Green, Esq.

[57] ABSTRACT

The present invention relates to a mutant cDNA sequence encoding the regulatory p85α subunit of phosphatidylinositol 3-kinase (PI3K), a method of detecting a mutation in the gene encoding the regulatory p85α subunit of phosphatidylinositol 3-kinase, as well as a diagnostic composition and a test kit for use in the method.

20 Claims, No Drawings

MUTANT CDNA ENCODING THE P85α SUBUNIT OF PHOSPHATIDYLINOSITOL 3-KINASE

CROSS-REFERENCE TO RELATED APPLICATIONS

This application claims priority of Danish application 0539/96 filed May 6, 1996, the contents of which are fully incorporated herein by reference.

FIELD OF THE INVENTION

The present invention relates to a mutant cDNA sequence encoding the regulatory p85α subunit of phosphatidylinositol 3-kinase (PI3K), a method of detecting a mutation in the gene encoding the regulatory p85α subunit of phosphatidylinositol 3-kinase, as well as a diagnostic composition and a test kit for use in the method.

BACKGROUND OF THE INVENTION

Phosphatidylinositol 3-kinase is a heterodimeric protein consisting of a catalytic 110 kDa subunit and an (α-85 kDa subunit that is necessary for docking to growth factor plasma membrane receptors including the insulin receptor and to signalling phosphotyrosine motifs in signalling proteins, e.g. insulin receptor substrate-1 (1,2). In addition to its association with receptors that mediate their effects via tyrosine kinase activity, PI 3-kinases are also implicated in facilitating membrane trafficking processes. The pinocytic activity, membrane ruffling and actin reorganization response observed when KB cells are exposed to insulin have been shown to be due to PI3-kinase activation (3,4). PI3-kinase has been implicated as a key intermediate in the cytoskeletal rearrangements that accompany secretory processes in platelets, basophil and neutrophil cells (5,6). Similarly, the yeast homologue VPS34 has been shown to be involved in vesicle trafficking and protein sorting (7). PI3-kinase is thus an attractive candidate protein as a mediator of insulin action on glucose transport as it could act as a point of convergence of signalling and trafficking processes.

In our attempts to elucidate the genetics of insulin action and glucose metabolism, we have performed mutational analysis on the regulatory p85α subunit of PI3K which is expressed in skeletal muscle.

References

1. Hiles, I. D., Otsu, M., Volinia, S., Fry, M. J., Gout, I., Dhand, R., Panayotou, G., Ruiz-Larrea, F., Thompson, A., Totty, N. F., Hsuan, J. J., Courtneige, S. A., Parker, P. J., and Waterfield, M. D. (1992) Cell 70, 419–429.
2. Myers, M. G., and White, M. F. (1993) Diabetes 42, 643–650.
3. Kotani, K., Yonezawa, K., Hara, K., Ueda, H., Kitamura, Y., Sakaue, H., Ando, A., Chavanieu, A., Calas, b., Grigorescu, f., Nishiyama, M., Waterfield, m.d., and Kasuga, M.(1994) EMBO J. 13, 2313–2321.
4. Kotani, K., Hara, K., Kotani, K., Yonezawa, K., and Kasuga, M. (19995) Biochem. Biophys. Res. Comm. (in press).
5. Yatomi, Y., Hazeki, O., Kume, S., and Ui, M. (11111992) Biochem. J. 285, 745–751.
6. Yano, H., Nakanishi, S., Kimura, K., Hanai, N., Saiitoh, Y., Fukui, Y., Nomomura, Y., and Matsuda, Y. (1993) J. Biol. Chem. 268, 25846–25856.
7. Schu, P. V., Kaoru, T., Fry, M. J., Stack, J. H., Waterfield, M. D., and Emr, S. D. (1993) Science 260, 88–91.

SUMMARY OF THE INVENTION

The gene encoding the regulatory p85α subunit of phosphatidylinositol 3-kinase has been examined for genetic variations which might be associated with or causing impaired insulin sensitivity, impaired glucose effectiveness, and/or impaired glucose disappearance.

The present invention relates to a nucleic acid sequence comprising a DNA sequence encoding the regulatory p85α subunit of human phosphatidylinositol 3-kinase (PI3K), the DNA sequence containing a mutation of at least one nucleotide, or comprising a segment of the cDNA sequence including said mutation. It has been found that such mutations may be localized to the p85α subunit of PI3K.

It has been found that mutation of the regulatory p85α subunit of PI3K gene may be indicative of abnormalities significant for the development of changes in whole body glucose metabolism and whole body insulin action. For instance, the mutation may give rise to the substitution of an amino acid in the regulatory p85α subunit of PI3K which may cause changes in the structure, such as the tertiary structure, or biochemical properties of the regulatory p85α subunit of PI3K. Such changes may interfere with the normal binding of the regulatory p85α subunit of PI3K to the insulin receptor kinase and insulin receptor substrates, e.g. IRS-1 and IRS-2 leading to altered glucose metabolism and reduced insulin sensitivity, and may lead to the development of insulin resistant conditions, such as NIDDM, cardiovascular diseases, obesity, and hypertension in human beings and other mammals.

In another aspect, the present invention relates to a living system containing a nucleic acid sequence of the invention and capable of expressing the regulatory p85α subunit of PI3K wherein at least one amino acid is substituted, inserted or deleted, or the living system contains a nucleic acid sequence of the invention carrying at least one silent mutation. The living system, which may comprise a cell or a multicellular organism containing the appropriate signal transduction pathway, may be used to screen for substances which have an effect on the regulatory p85α subunit of PI3K activity.

In a further aspect, the present invention relates to a method of detecting the presence of a mutation in the gene encoding the regulatory p85α subunit of PI3K, the method comprising obtaining a biological sample from a subject and analyzing the sample for a mutation of at least one nucleotide. It has now been shown that homozygous carriers of a the regulatory p85α subunit of PI3K mutation G to A in nucleotide #1020 exhibit a decreased glucose disappearance rate and a decreased glucose effectiveness and a decreased insulin sensitivity. Therefore, the present method is useful in diagnosing predisposition to insulin resistance and possibly impaired glucose tolerance and related diseases, such as NIDDM, cardiovascular diseases, obesity, and hypertension, in a subject as well as other disorders resulting from an altered glucose metabolism. Biological samples may, for instance, be obtained from blood, serum, plasma or tissue. The invention further relates to a diagnostic composition and a test kit for use in the method.

DETAILED DESCRIPTION OF THE INVENTION

Examples of specific mutations found in the cDNA sequence encoding the regulatory p85α subunit of PI3K are:

C to T in nucleotide #261;

T to G in nucleotide #663;

A to G in nucleotide #810;
G to A in nucleotide #1020
according to the numbering of E. Y. Skolnik et al., Cell 65, 1991, pp. 83–90 for the sequence (SEQ ID NO: 1):
5'-TACAACCAGGCTCAACTGTTGCATGGTAGCAGA-
TTTGCAAACATGA GTGCTGAGGGGTACCAGTA-
CAGAGCGCTGTATGATTATAAAAGG AAA-
GAGAAGAAGATATTGACTTGCACT-
TGGGTGACATATTGACTGTGA
ATAAAGGGTCCTTAGTAGCTCTTGGAT-
TCAGTGATGGACAGGAAGCCAGG CCTGAA-
GAAATTGGCTGGTTAAATGGCTATAAT-
GAAACCACAGGGGAAAGGGG
GGACTTTCCGGGAACTTACGTA-
GAATATATTGGAAGGAAAAAAATCTCGCCTCC
CACACCAAAGCCCCGGCCACCTCGGC-
CTCTTCCTGTTGCACCAGGTTCTTCGAA AACT-
GAAGCAGATGTTGAACAA-
CAAGCTTTGACTCTCCCGGATCTTGCAGAGCA
GTTTGCCCCTCCTGACATTGCCCCGC-
CTCTTCTTATCAAGCTCGTGGAAGCCATT
GAAAAGAAAGGTCTGGAATGTTCAACTC-
TATACAGAACACAGAGCTCCAGCAA CCTG-
GCAGTACGACAGCTTCTTGATTGTGATA-
CACCCTCCGTGGACTTGGAAAT
GATCGATGTGCACGTTTTGGCT-
GACGCTTTCAAACGCTATCTCCTGGACTTACCA
AATCCTGTCATTCCAGCAGCCGTTTA-
CAGTGAAATGATTTCTTTAGCTCCAGA AGTA-
CAAAGCTCCGAAGAATATATTCAGCTAT-
TGAAGAAGCTTATTAGGTCGCC
TAGCATACCTCATCAGTATTGGCT-
TACGCTTCAGTATTTGTTAAAACATTTCTTCAA
GCTCTCTCAAACCTCCAGCAAAAATCT-
GTTGAATGCAAGAGTACTCTCTGAAAT
TTTCAGCCCTATGCTTTTCAGATTCT-
CAGCAGCCAGCTCTGATAATACTGAAAA CCT-
CATAAAAGTTATAGAAATTTTAATCT-
CAACTGAATGGAATGAACGACAGCCTG
CACCAGCACTGCCTCCTAAACCAC-
CAAAACCTACTACTGTAGCCAACAACGGTA
TGAATAACAATATGTCCTTACAAAAT-
GCTGAATGGTACTGGGGAGATATCTCGAG GGAA-
GAAGTGAATGAAAAACTTCGAGATACAG-
CAGACGGGACCTTTTTGGTACG
AGATGCGTCTACTAAAATGCATGGTGAT-
TATACTCTTACACTAAGGAAAGGGGGAA ATAA-
CAAATTAATCAAAATATTTCATC-
GAGATGGGAAATATGGCTTCTCTGACCCA
TTAACCTTCAGTTCTGTGGTTGAAT-
TAATAAACCACTACCGGAATGAATCTCTAG
CTCAGTATAATCCCAAATTGGATGT-
GAAATTACTTTATCCAGTATCCAAATACCA ACAG-
GATCAAGTTGTCAAAGAAGATAATAT-
TGAAGCTGTAGGGAAAAAATTACAT
GAATATAACACTCAGTTTCAA-
GAAAAAAGTCGAGAATATGATAGAT-
TATATGAAGA ATATACCCGCACATCCCAG-
GAAATCCAAATGAAAAGGACAGCTATTGAAGC-
ATTTA ATGAAACCATAAAATATTTTGAAGAA-
CAGTGCCAGACCCAAGAGCGGTACAGCA
AAGAATACATAGAAAGTTTAAACGT-
GAAGGCAATGAGAAAGAAATACAAAGGA TTAT-
GCATAATTATGATAAGTTGAAGTCTC-
GAATCAGTGAAATTATTGACAGTAG
AAGAAGATTGGAAGAAGACTTGAAGAAG-
CAGGCAGCTGAGTATCGAGAAATTGA CAAACG-
TATGAACAGCATTAAACCAGACCTTATC-
CAGCTGAGAAAGACGAGAG
ACCAATACTTGATGTGGTTGACT-
CAAAAAGGTGTTCGGCAAAAGAAGTTGAACG
AGTGGTTGGGCAATGAAAACACTGAA-
GACCAATATTCACTGGTGGAAGATGATG
AAGATTTGCCCCATCATGATGAGAAGA-
CATGGAATGTTGGAAGCAGCAACCGAAA
CAAAGCTGAAAACCTGTTGCGAGG-
GAAGCGAGATGGCACTTTTCTTGTCCGGGA CAG-
CAGTAAACAGGGCTGCTATGCCTGCTCT-
GTAGTGGTGGACGGCGAAGTAAA
GCATTGTGTCATAAACAAAACAG-
CAACTGGCTATGGCTTTGCCGAGCCCTATAA
CTTGTACAGCTCTCTGAAAGAACTGGT-
GCTACATTACCAACACACCTCCCTTGT GCAGCA-
CAACGACTCCCTCAATGTCACACTAGC-
CTACCCAGTATATGCACAGCA
GAGGCGATGAAGCGCTTACTCTTTGATC-
CTTCTCCTGAAGTTCAGCCACCCTGA GGC-
CTCTGGAAAGCAAAGGGCTCCTCTC-
CAGTCTGATCTGTGAATTGAGCTGCA
GAAACGAAGCCATCTTTCTTTGGATGG-
GACTAGAGCTTTCTTTCACAAAAAAGA
AGTAGGGGAAGACATGCAGCCTAAGGCT-
GTATGATGACCACACGTTCCTAAGCT
GGAGTGCTTATCCCTTCTTTTTCTTTTTTTCT-
TTGGTTTAATTTAAAGCCACAACC
ACATACAACACAAAGAGAAAAAGAAATGCAAA-
3'.

It is at present assumed that mutations giving rise to substitutions of one or more amino acids in the regulatory p85α subunit of PI3K may be of particular importance as they may cause changes in the tertiary structure of the regulatory p85α subunit of PI3K and thereby change its biological activity. Consequently, in a particular embodiment, the present invention relates to a nucleic acid sequence comprising a cDNA sequence encoding the regulatory p85α subunit of PI3K and containing a mutation giving rise to at least one amino acid substitution in the regulatory p85α subunit of PI3K protein sequence. The mutation may for instance be located at a site where the amino acid substitution interferes with the binding of the regulatory p85α subunit of PI3K to insulin receptor kinase or insulin signalling proteins, e.g. IRS-1 and/or IRS-2, as such a mutation is most likely to be involved in changes in insulin signalling and basal and insulin stimulated glucose uptake. Such changes may therefore lead to reductions in whole body insulin sensitivity and whole body glucose metabolism. Martin, B. C. et al. (Lancet 1992, Vol. 340, 925–929) have previously shown that individuals having low or reduced Si (insulin sensitivity) or Sg (glucose effectiveness) have an increased risk of developing NIDDM.

Preferably such a DNA sequence is one containing a mutation of G to A in the third position of codon 326 of the regulatory p85w subunit of PI3K gene such that methionine$^{326}$ is substituted by isoleucine. This mutation is at a domain boundary, directly in front of an SH2 domain of p85α. The region is located downstream of a hydrophobic region the function of which is not known but which might be membrane-associated, as the subunit apparently acts as an adaptor allowing the kinase to associate with the membrane. FIG. 1 is a diagram of the PI3K p85α that shows the position of the codon326 mutation relative to an SH2 domain.

Apart from the missense mutations leading to substitution of one or more amino acids in the regulatory p85α subunit of PI3K protein, it is expected that silent mutations in the form of silent single nucleotide substitutions may have an influence on splicing (if it is located within a few bases of the exon-intron boundary), mRNA stability (if it changes the folding or the accessibility of the mRNA to RNAses), or protein stability (since codons may be changed into rare codons which may be translated more slowly and thereby influence the folding/stability of the protein (cf. Ikemura, T. and Ozeki, H.: Codon usage and transfer RNA contents: organism-specific codon-choice patterns in preference to the isoacceptor contents. *Cold Spring Harbor Symp. Quant. Biol.* 47:1087–1096, 1982; Grosjean, F. and Fiers, W.: Preferential codon usage in prokaryotic genes: the optimal codon-anticodon interaction energy and the selective codon usage in efficiently expressed genes. *Gene* 18:199–209, 1982). Such silent mutations may also be correlated with other important genetic changes and may therefore be useful as markers for detection of important genetic variants.

The length of the nucleic acid sequence of the invention, such as a cDNA isolate, may vary widely depending on the intended use. For use as an oligonucleotide probe for hybridisation purposes, the cDNA segment may be as short as 17 nucleotides. For expression in a living system as defined above, the cDNA isolate will typically comprise the full-length cDNA sequence encoding the regulatory p85α subunit of PI3K.

The nucleic acid sequence of the invention comprising the mutation in the cDNA sequence encoding the regulatory p85α subunit of PI3K may suitably be of genomic or cDNA origin, for instance obtained by preparing a genomic or cDNA library and screening for DNA sequences coding for all or part of the regulatory p85α subunit of PI3K by hybridization using synthetic oligonucleotide probes in accordance with standard techniques (cf. Sambrook et al., *Molecular Cloning: A Laboratory Manual*, 2nd Ed., Cold Spring Harbor, 1989). The probes used should be specific for the mutation. Alternatively, the DNA sequence encoding wild-type of the regulatory p85α subunit of PI3K may be modified by site-directed mutagenesis using synthetic oligonucleotides containing the mutation for homologous recombination in accordance with well-known procedures.

The DNA sequence may also be prepared by polymerase chain reaction (PCR) using specific primers, for instance as described in U.S. Pat. No. 4,683,202, Saiki et al., *Science* 239, 1988, pp. 487–491, or *PCR Protocols*, 1990, Academic Press, San Diego, Calif., USA.

The DNA isolate of the invention may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed and ligated. This procedure may preferably be used to prepare shorter segments of the regulatory p85α subunit of PI3K encoding DNA sequence.

The recombinant vector into which the DNA isolate is inserted may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated (e.g. a viral vector).

The recombinant vector is preferably an expression vector in which the DNA sequence encoding the regulatory p85α subunit of PI3K mutant is operably connected to additional segments required for transcription of the DNA. In general, the vector is derived from plasmid or viral DNA or may contain elements of both. The term "operably linked" indicates that the segments are arranged so that they function in concert for their intended purposes, e.g. transcription initiates in a promoter and proceeds through the DNA sequence coding for the regulatory p85α subunit of PI3K.

The promoter may be any DNA sequence which shows transcriptional activity in the host cell of choice and may be derived from genes encoding proteins either homologous or heterologous to the host cell. Examples of suitable promoters for directing the transcription of the mutant DNA encoding the regulatory p85α subunit of PI3K in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter.

The mutant DNA sequence encoding the regulatory p85α subunit of PI3K may also be operably connected to a suitable terminator, such as the human growth hormone terminator (Palmiter et al., op. cit.). The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector may further comprise a DNA sequence enabling the vector to replicate in the host cell in question. An example of such a sequence is the SV40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for the regulatory p85α subunit of PI3K, the promoter and the terminator, respectively, and to insert them into suitable vectors containing the information necessary for replication, are well known to persons skilled in the art (cf., for instance, Sambrook et al., op.cit.).

In a further aspect, the present invention relates to a variant of the regulatory p85α subunit of PI3K containing at least one amino acid substitution, in particular a variant containing at least one amino acid substitution at a site where the substitution interferes with the binding of the regulatory p85α subunit of PI3K to insulin receptor kinase or insulin signalling proteins, e.g. IRS-1 and/or IRS-2, or a fragment thereof including said substitution. Examples of such variants are variants in which methionine$^{326}$ is substituted by isoleucine.

The living system into which the DNA isolate of the invention is introduced may be a cell which is capable of producing the regulatory p85α subunit of PI3K and which has the appropriate signal transduction pathways. The cell is preferably a eukaryotic cell, such as a vertebrate cell, e.g. a *Xenopus laevis* oocyte or mammalian cell, in particular a mammalian cell. Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, J. Mol. Biol. 159 (1982), 601–621; Southern and Berg, J. Mol. Appl. Genet. 1 (1982), 327–341; Loyter et al., Proc. Natl. Acad. Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841–845.

The mutant DNA sequence encoding the regulatory p85α subunit of PI3K may then be expressed by culturing a cell as described above in a suitable nutrient medium under conditions which are conducive to the expression of the regulatory p85α subunit of PI3K-coding DNA sequence. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

The living system according to the invention may also comprise a transgenic animal. A transgenic animal is one in whose genome a heterologous DNA sequence has been introduced. In particular, the transgenic animal is a transgenic non-human mammal, mammals being generally provided with appropriate signal transduction pathways. For the present purpose, it is generally preferred to employ smaller mammals, e.g. rabbits or rodents such as mice or rats.

For expression of the mutant regulatory p85α subunit of PI3K gene of the invention in transgenic animals, a DNA sequence encoding the mutant regulatory p85α subunit of PI3K is operably linked to additional DNA sequences required for its expression to produce expression units. Such additional sequences include a promoter as indicated above, as well as sequences providing for termination of transcription and polyadenylation of mRNA. Construction of the expression unit for use in transgenic animals may conveniently be done by inserting a mutant DNA sequence encoding the regulatory p85α subunit of PI3K into a vector containing the additional DNA sequences, although the expression unit may be constructed by essentially any sequence of ligations.

The expression unit is then introduced into fertilized ova or early-stage embryos of the selected host species. Introduction of heterologous DNA may be carried out in a number of ways, including microinjection (cf. U.S. Pat. No. 4,873,191), retroviral infection (cf. Jaenisch, Science 240, 1988, pp. 1468–1474) or site-directed integration using embryonic stem cells (reviewed by Bradley et al., Bio/Technology 10, 1992, pp. 534–539). The ova are then implanted into the oviducts or uteri of pseudopregnant females and allowed to develop to term. Offspring carrying the introduced DNA in their germ line can pass the DNA on to their progeny, allowing the development of transgenic populations.

General procedures for producing transgenic animals are known in the art, cf. for instance, Hogan et al., *Manipulating the Mouse Embryo: A Laboratory Manual*, Cold Spring Harbor Laboratory, 1986; Simons et al., Bio/Technology 6, 1988, pp. 179–183; Wall et al., Biol. Reprod. 32, 1985, pp. 645–651; Buhler et al., Bio/Technology 8, 1990, pp. 140–143; Ebert et al., Bio/Technology 6: 179–183, 1988; Krimpenfort et al., Bio/Tecnology 9: 844–847, 1991, Wall et al., J. Cell. Biochem. 49: 113–120, 1992; U.S. Pat. No. 4,873,191, U.S. Pat. No. 4,873,316; WO 88/00239, WO 90/05188; WO 92/11757 and GB 87/00458. Techniques for introducing heterologous DNA sequences into mammals and their germ cells were originally developed in the mouse. See, e.g. Gordon et al., Proc. Natl. Acad. Sci. USA 77: 7380–7384, 1980, Gordon and Ruddle, Science 214: 1244–1246, 1981; Palmiter and Brinster, Cell 41: 343–345, 1985; Brinster et al., Proc. Natl. Acad. Sci. USA 82: 4438–4442, 1985; and Hogan et al. (ibid.). In brief, in the most efficient route used to date in the generation of transgenic mice, several hundred linear molecules of the DNA of interest are injected into one of the pro-nuclei of a fertilized egg according to techniques which have become standard in the art. Injection of DNA into the cytoplasm of a zygote can also be employed. Similar procedures may be employed to produce transgenic individuals of other species.

In one embodiment of the present method of detecting the presence of a mutation in the regulatory p85α subunit of PI3K gene, a biological sample is obtained from a subject, DNA (in particular genomic DNA) is isolated from the sample and digested with a restriction endonuclease which cleaves DNA at the site of the mutation, and cleavage of the DNA within the gene encoding the regulatory p85α subunit of PI3K at this site is determined. After digestion, the resulting DNA fragments may be subjected to electrophoresis on an agarose gel. DNA from the gel may then be blotted onto a nitrocellulose filter and hybridised with a radiolabelled probe. The probe may conveniently contain a DNA fragment of the regulatory p85α subunit of PI3K gene spanning the mutation (subtantially according to the method of E. M. Southern, *J. Mol. Biol.* 98, 1975, pp. 503, e.g. as described by B. J. Conner et al., *Proc. Natl. Acad. Sci. USA* 80, 1983, pp. 278–282).

In a variant of this embodiment, the DNA isolated from the sample may be amplified prior to digestion with the restriction endonuclease. Amplification may suitably be performed by polymerase chain reaction (PCR) using oligonucleotide primers based on the appropriate sequence of the regulatory p85α subunit of PI3K spanning the site(s) of mutation, essentially as described by Saiki et al., *Science* 230, 1985, pp. 1350–1354. After amplification, the amplified DNA may be digested with the appropriate restriction endonuclease and subjected to agarose gel electrophoresis. The restriction pattern obtained may be analyzed, e.g. by staining with ethidium bromide and visualising bands in the gel by means of UV light. As a control, wild-type DNA encoding the regulatory p85α subunit of PI3K (i.e. not containing the mutation) may be subjected to the same procedure, and the restriction patterns may be compared.

In the method of the invention, the sample is preferably analyzed for a mutation located at a site where amino acid substitution interferes with the binding of the regulatory p85α subunit of PI3K to insulin receptor kinase or insulin signalling proteins, e.g. IRS-1 and/or IRS-2. We have found that such a mutation is the mutation of G to A in the third position of codon 326 of the gene encoding the regulatory p85α subunit of PI3K.

A further embodiment of the method of the invention is an adaptation of the method described by U. Landegren et al., *Science* 241, 1988, pp. 1077–1080, which involves the ligation of adjacent oligonucleotides on a complementary target DNA molecule. Ligation will occur at the junction of the two oligonucleotides if the nucleotides are correctly base paired.

In a still further embodiment of the present method, the DNA isolated from the sample may be amplified using oligonucleotide primers corresponding to segments of the gene coding for the regulatory p85α subunit of PI3K. The amplified DNA may then be analyzed by hybridisation with a labelled oligonucleotide probe comprising a DNA sequence corresponding to at least part of the gene encoding the regulatory p85α subunit of PI3K and containing a mutation of at least one nucleotide, which mutation corresponds to the mutation the presence of which in the gene encoding the regulatory p85α subunit of PI3K is to be detected. As a control, the amplified DNA may furthermore be hybridised with a labelled oligonucleotide probe comprising a DNA sequence corresponding to at least part of the wild-type gene encoding the regulatory p85α subunit of PI3K. This procedure is, for instance, described by DiLella et al., Lancet 1, 1988, pp. 497–499. Other PCR-based methods which may be used in the present invention are the allele-specific PCR method described by R. Saiki et al., Nature 324, 1986, pp. 163–166, or D. Y. Wu et al., Proc. Natl. Acad. Sci. USA 86, 1989, pp. 2757–2760, which uses primers specific for the mutation in the regulatory p85α subunit of PI3K gene; the ligase chain reaction; restriction generating PCR; oligo nucleotide ligation assay; mini-sequencing; primer extension; and the heteroduplex method, cf. Landegren, U. (ed.) Laboratory Protocols for Mutation Detection. Oxford University Press, 1996.

Other methods of detecting mutations in DNA are reviewed in U. Landegren, GATA 9, 1992, pp. 3–8. A currently preferred method of detecting mutations is by single stranded conformation polymorphism (SSCP) analysis substantially as described by Orita M, Ivahana H, Kanazawa H, Hayashi K, Sekiya T: Detection of polymorphisms of human DNA by gel electrophoresis as single stranded conformational polymorphisms. Proc Natl Acad Sci 86:2766–70, 1989, or Orita et al., Genomics 5, 1989, pp. 874–879.

The label substance with which the probe is labelled is preferably selected from the group consisting of enzymes, coloured or fluorescent substances, or radioactive isotopes.

Examples of enzymes useful as label substances are peroxidases (such as horseradish peroxidase), phosphatases (such as acid or alkaline phosphatase), β-galactosidase, urease, glucose oxidase, carbonic anhydrase, acetylcholinesterase, glucoamylase, lysozyme, malate dehydrogenase, glucose-6-phosphate dehydrogenase, β-glucosidase, proteases, pyruvate decarboxylase, esterases, luciferase, etc.

Enzymes are not in themselves detectable but must be combined with a substrate to catalyse a reaction the end product of which is detectable. Examples of substrates which may be employed in the method according to the invention include hydrogen peroxide/tetramethylbenzidine or chloronaphthole or o-phenylenediamine or 3-(p-hydroxyphenyl) propionic acid or luminol, indoxyl phosphate, p-nitrophenylphosphate, nitrophenyl galactose, 4-methyl umbelliferyl-D-galactopyranoside, or luciferin.

Alternatively, the label substance may comprise coloured or fluorescent substances, including gold particles, coloured or fluorescent latex particles, dye particles, fluorescein, phycoerythrin or phycocyanin.

In a particularly favoured embodiment, the probe is labelled with a radioactive isotope. Radioactive isotopes which may be used for the present purpose may be selected from I-125, I-131, I-111, H-3, P-32, C-14 or S-35. The radioactivity emitted by these isotopes may be measured in a beta- or gamma-counter or by a scintillation camera in a manner known per se.

For use in the present method, the invention further relates to a test kit for detecting the presence of a mutation in the gene encoding the regulatory p85α subunit of PI3K, the kit comprising (a) a restriction endonuclease which cleaves DNA at the site of the mutation,
(b) a first DNA sequence corresponding to at least part of the wild-type gene encoding the regulatory p85α subunit of PI3K and/or
(c) a second DNA sequence corresponding to at least part of the gene encoding the regulatory p85α subunit of PI3K and containing a mutation of at least one nucleotide, which mutation corresponds to the mutation the presence of which in the gene encoding the regulatory p85α subunit of PI3K is to be detected. Said mutation is preferably the codon326 mutation resulting in a methionin to isoleucin substitution.

The first DNA sequence may, for instance, be obtained from genomic DNA or cDNA encoding the regulatory p85α subunit of PI3K obtained from a healthy subject (a non-mutation carrier). The second DNA sequence may conveniently be a DNA construct according to the invention.

For use in the present method, the invention further relates to a test kit for detecting the presence of a mutation in the gene encoding the regulatory p85α subunit of PI3K, the kit comprising (a) means for amplifying DNA, and
(b) a labelled oligonucleotide probe comprising a DNA sequence corresponding to at least part of the gene encoding the regulatory p85α subunit of PI3K and containing a mutation of at least one nucleotide, which mutation corresponds to the mutation the presence of which in the gene encoding the regulatory p85α subunit of PI3K is to be detected. Preferably, the mutation the presence of which is to be detected is the codon 326 methionin to isoleucin mutation of p85α.

Appropriate means for amplifying DNA (typically genomic DNA isolated from the biological sample) include, for instance, oligonucleotide primers, appropriate buffers and a thermostable DNA polymerase.

The kit may further comprise a labelled oligonucleotide probe comprising a DNA sequence corresponding to at least part of the wild-type gene encoding the regulatory p85α subunit of PI3K.

The invention also relates to the use of a nucleic acid sequence of the invention or a segment thereof as a probe, preferably an oligonucleotide probe, for detection of the presence of a mutation in a regulatory subunit, preferably the p85α subunit or any isoform or homologous polypeptide thereof, of PI3K, the regulatory subunit being preferably isolated from a biological sample obtained from a subject.

The invention is further illustrated in the following example which is not intended in any way to limit the scope of the invention as claimed.

EXAMPLE

Subjects. For studies of intravenous glucose and tolbutamide stimulated serum insulin and C-peptide release 380 study participants were randomly recruited from a population of young individuals aged 18–32 years, who in 1979/80 and again in 1984/85 as children had participated in blood pressure surveys in a representative and specified part of Copenhagen City. All were Danish Caucasians by self-identification. Physiological characteristics and other genetic analyses obtained in the present population sample have been presented previously, cf. Clausen et al. The Lancet 346:397–402, 1995. Prior to the participation in the study informed consent was obtained for all subjects. The study was approved by the Ethical Committee of Copenhagen and was in accordance with the principles of the Declaration of Helsinki.

Measurements of glucose disappearance constant (Kg), insulin sensitivity (Si) and glucose effectiveness (Sg). Each subject underwent an intravenous glucose tolerance test (IVGTT) after a 12 h overnight fasting period. Baseline values of serum insulin, serum C-peptide and plasma glucose were taken in duplicate with 5 min intervals. Glucose was injected i.v. in the contralateral antecubital vein over a period of 1 min (0.3 g/kg body weight of 50% glucose). At 20 min following the end of the glucose injection, a bolus of 3 mg tolbutamide/kg body weight (Rastinon, Hoechst, Germany) was injected during 5 sec to elicit a secondary pancreatic beta cell response. Venous blood was sampled at 2, 4, 8, 19, 22, 30, 40, 50, 70, 90, 180 min, timed from the end of the glucose injection for measurements of plasma glucose, serum insulin and serum C-peptide. All the IVGTT's were done by the same investigator. Glucose induced acute serum insulin and C-peptide responses (0–8 min) were calculated by means of the trapezoidal rule as the incremental values (area under the curve when expressed above basal values). Insulin sensitivity indeks (Si) and glucose effectiveness (Sg) were calculated using the Bergman MINMOD computer program developed specifically for the combined intravenous glucose and tolbutamide tolerance test, cf. Clausen et al. op cit. Intravenous glucose disappearance constant (Kg) was calculated as the slope of the line relating the natural logarithm of the glucose concentration to the time between 8 and 19 minutes after the glucose bolus. Plasma concentrations of glucose, serum specific insulin and serum C-peptide were measured as described.

Chemical analysis. Chemical analyses were performed as described previously (cf. Almind K, Bjorbxk C, Vestergaard H, Hansen T, Echwald S, Pedersen O: Amino acid polymorphisms of insulin receptor substrate-1 in non-insulin-dependent diabetes mellitus. *The Lancet* 342:828–32, 1993). Briefly, measurements of glucose in plasma was done by a hexokinase method and serum C-peptide concentrations were analyzed by RIA.

Isolation of genomic DNA from whole blood. Genomic DNA was isolated from human leucocyte nuclei isolated from whole blood by digestion with proteinase K followed by phenol extraction on an Applied Biosystems 341 Nucleic Acid Purification System (Applied Biosystems Inc., Foster City, Calif., USA)

Muscle biopsies. Needle biopsies of the vastus lateralis muscle (500 mg) from subjects were obtained during local anesthesia (1% Lidocaine, without epinephrine). A modified Bergstrom needle was used (Stille-Werner, Copenhagen Denmark), and samples were taken from about 20 cm above the knee. Biopsies were blotted to remove blood and connective tissue and frozen in liquid nitrogen within 30 seconds.

Preparation of total RNA from skeletal muscle. Muscle biopsies were thawed and homogenized in a 4 M guanidinium thiocyanate solution. Total RNA was isolated using a 394 RNA/DNA extractor (Applied Biosystems Inc., Foster City, Calif., USA). Purity and concentration of the samples were determined by measuring the 260/280 nm absorption ratio.

cDNA synthesis. cDNA was synthesized in volumes of 25 $\mu$l containing (in final concentrations) 50 mM Tris-HCl (pH 8.3), 75 mM KCl, 3 mM $MgCl_2$, 10 mM DDT, 0.2 mM dNTP's, 40 U Rnasin (Promega, Madison, Wis.), 0.625 $\mu$g Oligo $(dT)_{18}$, 400 U Molony murine leukemia virus reverse transcriptase (M-MLV RT) (Life Technologies, Grand Island, N.Y.), and 1.0 $\mu$g of total muscle RNA. The reactions were performed at 37° C. for 1 h, followed by enzyme inactivation for 10 min at 95° C. Samples were diluted to a final volume of 200 $\mu$l and stored at −20° C.

Oligonucleotides used for amplification. Oligonucleotides, 18–21 mers in length and with one or two G's and/or C's at the 3' end, were synthesized on an Applied Biosystems 394 DNA/RNA Synthesizer and applied to a NAB™-10 column (Pharmacia P-L Biochemicals Inc., Milwaukee, Wis.) and used without further purification. Biotin labelling of primers was done during synthesis using DMT-Biotin-C6-PA (Genosys Biotechnologies Inc., Great Britain). The human p85α has been published by Skolnik (Skolnik et al., 1991) (GenBank, Genetics Computer Group (Madison; Wis.), accession number M61906). The published amino acid sequence has 97% homology to bovine p85α cDNA (M61745), 95% to mouse p85α cDNA (M60651) and only 59% to bovine p85β cDNA (M61746). Primers for polymerase chain reaction (PCR) amplification of human p85α cDNA were designed from areas of the cDNA sequence, with low homology to bovine p85β (FIG. 2).

PCR amplification of cDNA. A primary PCR amplification was carried out with 5 $\mu$l cDNA as template. The assay conditions were: 10 mM Tris-HCl (pH 9.0), 50 mM KCl, 1.5 mM $MgCl_2$, 0.1% Triton X-100, 0.2 mM dNTP's, 0.2 $\mu$M of each oligonucleotide primer, and 0.6 U Taq DNA Polymerase (Promega, Madison, Wis.) (all in final concentrations and total colume of 25 $\mu$l). The mixture was overlaid with mineral oil and after initial denaturation at 95° C. for 4 min, the samples were subjected to 35 cycles of amplification: denaturation at 95° C. for 1 min, annealing at 55° C. for 1 min and extension at 72° C. for 2 min (Omnigene Thermocycler, Hybaid Limited, Middlesex, U.K.). A final step with 5 min extension at 72° C. was performed to ensure full-length segments.

Primary SSCP screening for variants in the regulatory p85α subunit of PI3K gene. The coding region of PI3K p85α subunit was scanned by PCR-SSCP at the nucleotide level. cDNA from 70 NIDDM patients and 12 healthy control subjects without any known family history of NIDDM was included in the primary SSCP screening. SSCP-analysis (according to the method of Orita et al., *Genomics* 5, 1989, pp. 874–879) was performed on DNA-segments of 250–300 bp with an overlap of 60 base pairs between segments. DNA-segments for SSCP analysis were PCR-amplified in a standard PCR-reaction, using specific primers as described above. PCR-reactions were performed as described above and 3 $\mu$l of the PCR-reaction was mixed with 12 $\mu$l of SSCP loading buffer (95% deionised formamide, 5% NaOH, xylene blue, bromo-phenol blue), and 2 $\mu$l were analyzed on a 38×31×0.04 cm, non-denaturing 5% acrylamide (49:1 acrylamide:bisacrylamide) gel in adjacent lanes. For heteroduplex formation samples were loaded after heating at 95° C. for 5 min. and subsequently incubating 15 min. on ice. Each DNA-segment was analyzed at two different gel conditions. A "cold gel", containing 1% glycerol, 1×TBE-buffer (90 mM Tris-Borate, 2.5 mM EDTA), and 5% acrylamide (49:1, acrylamide:bisacrylamide) was run at 8° C. in a cold-room for 3 to 5 h with an applied power of 35 watt. A "warm" gel containing 5% glycerol, 1×TBE-buffer (90 mM Tris-Borate, 2.5 mM EDTA), and 5% acrylamide (49: 1, acrylamide:bisacrylamide), was run at 24° C. for 3 to 4 h, applying 65 watt. The electrophoresis buffer was ½×TBE (45 mM Tris Base, 1.25 mM EDTA). The power supplies used were equipped with a temperature controlling device, to assure constant running temperature (Temperature Controller, Stratagene, La Jolla, Calif., USA). After electrophoresis, the gels were transferred to Whatman 3 MM filter paper, covered in plastic wrap, and autoradiografed at −80° C., for 3 h to 3 days using intensifying screens. Autoradiografies were analyzed visually to reveal variations in migration. SSCP screening and subsequent direct sequencing revealed 4 nucleotide variants, shown in Table 1 below.

TABLE 1

Localisation, character and genotype frequency of nucleotide variants in PI3K p85α subunit. The base number is calculated from first sequenced base (accession number M69106), the codon number is calculated from first coding methionin (code 1, base number 43-45, sequence accession number M69106).

| SSCP Segment | Set of Primers | Nucleotide Change Position/Base | Amino Acid Change Codon/a.a. | Genotype Frequency | NIDDM | Control |
|---|---|---|---|---|---|---|
| 2. | 3–4 | 261/C → T | 73/Tyr → Tyr | ho | 9 | 0 |
| | | | | he | 29 | 4 |
| | | | | wt | 32 | 8 |
| 4. | 7–8 | 663/T → G | 207/Ile → Ile | ho | 0 | 0 |
| | | | | he | 3 | 1 |
| | | | | wt | 67 | 11 |
| 4. | 7–8 | 810/A → G | 256/Lys → Lys | ho | 0 | 0 |
| | | | | he | 2 | 0 |
| | | | | wt | 68 | 12 |
| 5. | 9–10 | 1020/G → A | 326/Met → Met | ho | 1 | 0 |
| | | | | he | 5 | 1 |
| | | | | wt | 64 | 11 |

Primers used for PCR amplification of the codon 326 polymorphism for SSCP are listed in table 2. FIG. 2 shows the distribution of primers, primary and secondary segments in SSCP scanning of p85α. The numbers refer to the primer numbers in Table 2, e.g. (1–8) refers to the primers PI 1 through PI8 of Table 2.

TABLE 2

Nucleotide sequences of DNA primers used for PCR amplification to detect the regulatory p85α subunit of PI3K amino acid substitution at codon 326 by SSCP gel analysis

| NAME | SPEC (BIO) | GENE | SEQUENCE 5'–3' | BASE NUMBER | Concentration PMOL/μl |
|---|---|---|---|---|---|
| PI 1 SEQ ID NO: 2 | | P13K, P85 | caa cca ggc tca act gtt gc | 1 to 22 | 397 |
| PI 2 SEQ ID NO: 3 | | P13K, P85 | taa gtt ccc gga aag tcc cc | 240 to 60 | 402 |
| PI 3 SEQ ID NO: 4 | | P13K, P85 | gaa att ggc tgg tta aat ggc | 195 to 216 | 494 |
| PI 4 SEQ ID NO: 5 | | P13K, P85 | gag ctt gat aag aag agg cg | 437 to 447 | 359 |
| PI 5 SEQ ID NO: 6 | | P13K, P85 | gat ctt gca gag cag ttt gc | 390 to 410 | 496 |
| PI 6 SEQ ID NO: 7 | | P13K, P85 | acg gct gct gga atg aca gg | 628 to 647 | 407 |
| PI 7 SEQ ID NO: 8 | | P13K, P85 | tgg ctg acg ctt tca aac gc | 586 to 606 | 528 |
| PI 8 SEQ ID NO: 9 | | P13K, P85 | gaa tct gaa aag cat agg gc | 848 to 867 | 425 |
| PI 9 SEQ ID NO: 10 | | P13K, P85 | ag ctc tct caa acc tcc agc | 787 to 807 | 695 |
| PI 10 SEQ ID NO: 11 | | P13K, P85 | cga gat atc tcc cca gta cc | 1139 to 1157 | 757 |
| PI 11 SEQ ID NO: 12 | | P13K, P85 | ac tac tgt agc caa caa cgg | 984 to 1104 | 638 |
| PI 12 SEQ ID NO: 13 | | P13K, P85 | gtc aga gaa gcc ata ttt | 1203 to 1224 | 402 |
| PI 13 SEQ ID NO: 14 | | P13K, P85 | t tac act aag gaa agg ggg | 1143 to 1169 | 363 |
| PI 14 SEQ ID NO: 15 | | P13K, P85 | ga ttt ctt ggg atg tgc ggg | 1454 to 1473 | 337 |
| PI 15 SEQ ID NO: 16 | | P13K, P85 | cac tca gtt tca aga aaa aag tc | 1401 to 1424 | 629 |
| PI 16 SEQ ID NO: 17 | | P13K, P85 | gc ttc ttc aag tct tct tcc | 1677 to 1696 | 394 |
| PI 17 SEQ ID NO: 18 | | P13K, P85 | tga taa gtt gaa gtc tcg | 1627 to 1645 | 366 |
| PI 18 SEQ ID NO: 19 | | P13K, P85 | a tct tca tca tct tcc acc | 1870 to 1879 | 230 |

TABLE 2-continued

Nucleotide sequences of DNA primers used for PCR amplification to detect the regulatory p85α subunit of PI3K amino acid substitution at codon 326 by SSCP gel analysis

| NAME | SPEC (BIO) | GENE | SEQUENCE 5'–3' | BASE NUMBER | Concentration PMOL/μl |
|---|---|---|---|---|---|
| PI 19 SEQ ID NO: 20 | | P13K, P85 | ag ttg aac gag tgg ttg ggc | 1817 to 1836 | 418 |
| PI 20 | | P13K, P85 | g aaa gcc ata gcc agt tgc | 2068 to 2086 | 291 |
| PI 21 | | P13K, P85 | gg tgg acg gcg aag taa agc | 2029 to 2048 | 377 |
| PI 22 | | P13K, P85 | agc cct ttg ctt tcc aga gg | 2264 to 2283 | 335 |

Secondary screening for additional codon 326 mutation carriers. Additionally, in a random sample of unrelated, healthy young volunteers in whom an intavenous glucose tolerance test in combination with tolbutamide injection was performed, 263 wild-type (Wt), 109 heterozygous (He) and 8 homozygous (Ho) individuals were identified. Glucose disappearance constant (Kg) and glucose effectiveness (Sg) were significantly different among the groups (Kg: Wt $2.3\pm1.1\_10^{-2}$ min$^{-1}$, He $2.3\pm1.0$, Ho $1.4\pm0.6$ (mean±SD) (p=0.02); Sg: Wt $2.1\pm0.7\_10^{-2}$min$^{-1}$, He $2.2\pm0.6$, Ho $1.7\pm0.6$ (p=0.03)). No significant difference was observed in insulin sensitivity (Wt $15.3\pm9.5\_10^{-5}$ L min$^{-1}$ pmol$^{-1}$, He $15.1\pm8.6$, Ho $10.3\pm8.3$ (p=0.20)). Both Kg and Sg were significantly reduced among Ho subjects compared to the combined values for Wt and He carriers (p=0.004 and p=0.03, respectively). Moreover, in Ho carriers a 30% reduction in insulin sensitivity (p=0.08) was found. All homozygous subjects were validated using direct sequencing. It was concluded that in homozygous carriers the common codon $326^{Met\rightarrow Ile}$ variant of the p85α subunit of PI3K is associated with a decreased glucose disappearance constant possibly resulting in intravenous glucose tolerance and a decreased glucose effectiveness in young, healthy individuals.

Allele specific oligonucleotide hybridization: Genomic DNA (100 ng) was PCR amplified with primers 10 and 11 (FIG. 2) as described above except for addition of 2.0 mM MgCl$_2$ and 10% DMSO. The samples were subjected to 40 cycles of amplification: denaturation at 95° C. for 30 sec, annealing at 54° C. for 30 sec, extension at 72° C. for 30 sec and final extension for 5 min at 72° C. using GeneAmp PCR system 9600 (Perkin Elmer, Norwalk, Conn). PCR samples (15 μl) were denaturated in 85 μl 0.2 M NaOH, 1 M NaCl and 2×45 μl were transferred to Hybond-N$^+$ filters (Amersham, Buckinghamshire, Great Britain).

The membranes were crosslinked twice in a UV Stratalink (Stratagene, La Jolla, Calif.) at 1200×100 μJoule. Membranes were prehybridized for 1 hour in 6×SSPE, 5×Denhardt, 0% SDS and 100 μg/ml denaturated salmon sperm. Hybridization was performed with allele specific probes (wild type: 5' AAC AAT ATG TCC TTA CA SEQ ID NO: 24; variant 5' AAC AAT ATA TCC TTA CA SEQ ID NO: 25) for 3 hours in 6×SSPE, 5×Denhardt, 0. 1% SDS. Probes were 5'-end-labeled by T4-kinase (Promega, Madison, Wis.) as described (ref) using (Y-$^{32}$P) ATP (Amersham, Buckinghamshire, Great Britain). After hybidization membranes were washed for 2×0.5 h in 6×SSPE and 0.1% SDS at 45° C. for wild type probe and 41° C. for variant probe. Filters were applied to PhosphoImager Screens for 2–10 h and visualized on an ImageQuant, Phospholmager available from Molecular Dynamics.

Direct sequencing. SSCP-variants were sequenced using either an Automated Laser Fluorescence Sequencer (LKB Pharmnacia Uppsala, Sweden) and using Fluore-dATP (Pharmacia/Boeringer Mannheim) as label in the AutoRead Sequencing Kit (Pharmacia, Uppsala, Sweden), or by standard dideoxynucleotide sequencing using the Sequenase 2.0 (United States Biochemical Corporation, Cleveland, Ohio.) and ($\alpha$S$^{35}$) dATP (Amersham International plc, Buckinghamshire, Great Britain) according to protocols supplied by the producer.

DNA for sequencing was PCR-amplified using 5 pmol/100 μl reaction of one biotinylated primer, and single-stranded DNA was isolated using streptavidin-coated magnetic beads (Dynabeads, Oslo, Norway). DNA was sequenced as single stranded DNA according to protocols, using internal sequencing primers.

Statistics. Chi-square analysis was applied to test for significance of differences in allele and genotype frequencies. A non-parametric Kruskall-Wallis test or a Mann-Whitney test was used for comparison between groups. Data are means±SEM. A p-value<0.05 (two-tailed) was considered significant. Statistical Package of Social Science (SPSS) for Windows, version 6.01, was used for statistical analysis.

We claim:

1. An isolated nucleic acid sequence comprising (a) a DNA sequence encoding the p85α subunit of human phosphatidylinositol 3-kinase (PI3K), wherein the DNA sequence comprises a mutation selected from the group consisting of C to T in nucleotide 261, T to G in nucleotide 663, A to G in nucleotide 810; and G to A in nucleotide 1020 of SEQ ID NO:1, or (b) a segment of the DNA sequence including the mutation.

2. A recombinant vector comprising a nucleic acid sequence according to claim 1.

3. A cell comprising a vector according to claim 2.

4. The cell according to claim 3, wherein said cell is a mammalian cell line or is present in a transgenic animal.

5. A method of detecting the presence of a mutation in a gene encoding a regulatory subunit of PI3K, the method comprising obtaining a biological sample from a subject and analyzing the sample for the presence of a nucleic acid sequence according to claim 1.

6. The method according to claim 5, wherein a biological sample is obtained from a subject, DNA is isolated from the sample and digested with a restriction endonuclease which cleaves DNA at the site of the mutation, and cleavage of the DNA within the gene encoding the p85α regulatory subunit of PI3K at this site is determined.

7. The method according to claim 6, wherein the restriction pattern of the DNA after digestion with the restriction endonuclease is compared to the restriction pattern obtained with a negative control comprising at least a portion of wild-type DNA encoding the p85α regulatory subunit of PI3K.

8. The method according to claim 6, wherein the restriction pattern of the DNA after digestion with the restriction endonuclease is compared to the restriction pattern obtained with a positive control comprising at least a portion of DNA encoding the p85α regulatory subunit of PI3K and containing the mutation.

9. The method according to claim 8, wherein the positive control comprises a nucleic acid sequence comprising (a) a DNA sequence encoding a regulatory subunit of phosphatidylinositol 3-kinase (PI3K), wherein the DNA sequence comprises a mutation of at least one nucleotide, or (b) a segment of the DNA sequence including the mutation.

10. The method according to claim 6, which further comprises amplifying the DNA isolated from the sample prior to digestion with the restriction endonuclease.

11. The method according to claim 5, wherein a biological sample is obtained from a subject, DNA is isolated from the sample, the DNA is amplified and hybridised to a labelled oligonucleotide probe comprising a DNA sequence corresponding to at least part of the gene encoding a regulatory subunit of PI3K and containing a mutation of at least one nucleotide, which mutation corresponds to the mutation the presence of which in the gene is to be detected, and hybridisation of the probe to the DNA is determined.

12. The method according to claim 11, wherein the amplified DNA is further hybridized to a labelled oligonucleotide probe comprising a DNA sequence corresponding to at least part of the wild-type gene encoding a regulatory subunit of PI3K, and hybridisation of the probe to the DNA is determined.

13. The method according to claim 11, wherein the label substance with which the oligonucleotide probe containing the mutation is labelled is different from the label substance with which the oligonucleotide probe corresponding to the wild-type DNA is labelled.

14. The method according to claim 11, wherein the label is selected from the group consisting of enzymes, coloured or fluorescent substances, and radioactive isotopes.

15. A diagnostic composition for detecting the presence of a mutation in the gene encoding a regulatory subunit of PI3K, the composition comprising a nucleic acid sequence according to claim 1.

16. A test kit for detecting the presence of a mutation in the gene encoding the p85α subunit of human PI3K, wherein said mutation is selected from the group consisting of C to T in nucleotide 261, T to G in nucleotide 663, A to G in nucleotide 810; and G to A in nucleotide 1020 of SEQ ID NO:1, the kit comprising (a) a restriction endonuclease which cleaves DNA at the site of the mutation, (b) a first DNA sequence corresponding to at least part of the wild-type gene encoding the p85α subunit of human PI3K, and/or (c) a second DNA sequence corresponding to at least part of the gene encoding the p85α subunit of PI3K and containing a mutation of at least one nucleotide, which mutation corresponds to the mutation the presence of which in the gene is to be detected.

17. A test kit according to claim 16, which further comprises means for amplifying DNA.

18. A test kit comprising (a) means for amplifying DNA, and (b) a labelled oligonucleotide probe comprising a DNA sequence corresponding to at least part of the gene encoding the p85α subunit of human PI3K and containing a mutation of at least one nucleotide, wherein said mutation is selected from the group consisting of C to T in nucleotide 261, T to G in nucleotide 663, A to G in nucleotide 810; and G to A in nucleotide 1020 of SEQ ID NO:1.

19. The test kit according to claim 18, which further comprises a labelled oligonucleotide probe comprising a DNA sequence corresponding to at least part of the wild-type gene encoding PI3K.

20. The test kit according to claim 18, wherein the label is selected from the group consisting of enzymes, coloured or fluorescent substances, and radioactive isotopes.

* * * * *

SEQUENCE LISTING

<160> NUMBER OF SEQ ID NOS: 25

<210> SEQ ID NO 1
<211> LENGTH: 2508
<212> TYPE: DNA
<213> ORGANISM: human

<400> SEQUENCE: 1
tacaaccagg ctcaactgtt gcatggtagc agatttgcaa acatgagtgc tgaggggtac      60

```
cagtacagag cgctgtatga ttataaaaag gaaagagaag aagatattga cttgcacttg      120
ggtgacatat tgactgtgaa taaagggtcc ttagtagctc ttggattcag tgatggacag      180
gaagccaggc ctgaagaaat tggctggtta aatggctata atgaaaccac aggggaaagg      240
ggggactttc cgggaactta cgtagaatat attggaagga aaaaaatctc gcctcccaca      300
ccaaagcccc ggccacctcg gcctcttcct gttgcaccag gttcttcgaa aactgaagca      360
gatgttgaac aacaagcttt gactctcccg gatcttcag agcagtttgc ccctcctgac       420
attgccccgc ctcttcttat caagctcgtg gaagccattg aaaagaaagg tctgaatgt       480 tcaactctat acagaacaca gagctccagc aacctggcag tacgacagct tcttgattgt      540
gatacaccct ccgtggactt ggaaatgatc gatgtgcacg ttttggctga cgctttcaaa      600
cgctatctcc tggacttacc aaatcctgtc attccagcag ccgtttacag tgaaatgatt      660
tctttagctc cagaagtaca aagctccgaa gaatatattc agctattgaa gaagcttatt      720
aggtcgccta gcatacctca tcagtattgg cttacgcttc agtatttgtt aaaacatttc      780
ttcaagctct ctcaaacctc cagcaaaaat ctgttgaatg caagagtact ctctgaaatt      840
ttcagcccta tgcttttcag attctcagca gccagctctg ataatactga aaacctcata      900
aaagttatag aaattttaat ctcaactgaa tggaatgaac gacagcctgc accagcactg      960
cctcctaaac caccaaaacc tactactgta gccaacaacg gtatgaataa caatatgtcc     1020
ttacaaaatg ctgaatggta ctggggagat atctcgaggg aagaagtgaa tgaaaaactt     1080
cgagatacag cagacgggac cttttttggta cgagatgcgt ctactaaaat gcatggtgat     1140
tatactctta cactaaggaa agggggaaat aacaaattaa tcaaaatatt tcatcgagat     1200
gggaaatatg gcttctctga cccattaacc ttcagttctg tggttgaatt aataaaccac     1260
taccggaatg aatctctagc tcagtataat cccaaattgg atgtgaaatt actttatcca     1320
gtatccaaat accaacagga tcaagttgtc aagaagata atattgaagc tgtagggaaa      1380
aaattacatg aatataacac tcagtttcaa gaaaaaagtc gagaatatga tagattatat     1440
gaagaatata cccgcacatc ccaggaaatc caaatgaaaa ggacagctat tgaagcattt     1500
aatgaaacca taaatatttt tgaagaacag tgccagaccc aagagcggta cagcaaagaa     1560
tacatagaaa agtttaaacg tgaaggcaat gagaaagaaa tacaaaggat tatgcataat     1620
tatgataagt tgaagtctcg aatcagtgaa attattgaca gtagaagaag attggaagaa     1680
gacttgaaga agcaggcagc tgagtatcga gaaattgaca aacgtatgaa cagcattaaa     1740
ccagacctta tccagctgag aaagacgaga gaccaatact tgatgtggtt gactcaaaaa     1800
ggtgttcggc aaaagaagtt gaacgagtgg ttgggcaatg aaaacactga agaccaatat     1860
tcactggtgg aagatgatga agatttgccc catcatgatg agaagacatg gaatgttgga     1920
agcagcaacc gaaacaaagc tgaaaacctg ttgcgaggga gcgagatgg cacttttctt      1980 gtccgggaca gcagtaaaca gggctgctat gcctgctctg tagtggtgga cggcgaagta     2040
aagcattgtg tcataaacaa aacagcaact ggctatggct ttgccgagcc ctataacttg     2100
tacagctctc tgaaagaact ggtgctacat taccaacaca cctcccttgt gcagcacaac     2160
gactccctca atgtcacact agcctaccca gtatatgcac agcagaggcg atgaagcgct     2220
tactctttga tccttctcct gaagttcagc caccctgagg cctctggaaa gcaagggct      2280 cctctccagt ctgatctgtg aattgagctg cagaaacgaa gccatctttc tttggatggg     2340
actagagctt tcttttcacaa aaaagaagta ggggaagaca tgcagcctaa ggctgtatga    2400
tgaccacacg ttcctaagct ggagtgctta tcccttcttt ttcttttttt ctttggttta    2460
```

-continued atttaaagcc acaaccacat acaacacaaa gagaaaaaga aatgcaaa          2508

<210> SEQ ID NO 2
<211> LENGTH: 20
<212> TYPE: DNA
<213> ORGANISM: human

<400> SEQUENCE: 2
caaccaggct caactgttgc                                         20

<210> SEQ ID NO 3
<211> LENGTH: 20
<212> TYPE: DNA
<213> ORGANISM: human

<400> SEQUENCE: 3
taagttcccg gaaagtcccc                                         20

<210> SEQ ID NO 4
<211> LENGTH: 21
<212> TYPE: DNA
<213> ORGANISM: human

<400> SEQUENCE: 4
gaaattggct ggttaaatgg c                                       21

<210> SEQ ID NO 5
<211> LENGTH: 20
<212> TYPE: DNA
<213> ORGANISM: human

<400> SEQUENCE: 5
gagcttgata agaagaggcg                                         20

<210> SEQ ID NO 6
<211> LENGTH: 20
<212> TYPE: DNA
<213> ORGANISM: human

<400> SEQUENCE: 6
gatcttgcag agcagtttgc                                         20

<210> SEQ ID NO 7
<211> LENGTH: 20
<212> TYPE: DNA
<213> ORGANISM: human

<400> SEQUENCE: 7
acggctgctg gaatgacagg                                         20

<210> SEQ ID NO 8
<211> LENGTH: 20
<212> TYPE: DNA
<213> ORGANISM: human

<400> SEQUENCE: 8
tggctgacgc tttcaaacgc                                         20

<210> SEQ ID NO 9
<211> LENGTH: 20
<212> TYPE: DNA
<213> ORGANISM: human

<400> SEQUENCE: 9

-continued gaatctgaaa agcatagggc                       20

<210> SEQ ID NO 10
<211> LENGTH: 20
<212> TYPE: DNA
<213> ORGANISM: human

<400> SEQUENCE: 10
agctctctca aacctccagc                       20

<210> SEQ ID NO 11
<211> LENGTH: 20
<212> TYPE: DNA
<213> ORGANISM: human

<400> SEQUENCE: 11
cgagatatct ccccagtacc                       20

<210> SEQ ID NO 12
<211> LENGTH: 20
<212> TYPE: DNA
<213> ORGANISM: human

<400> SEQUENCE: 12
actactgtag ccaacaacgg                       20

<210> SEQ ID NO 13
<211> LENGTH: 18
<212> TYPE: DNA
<213> ORGANISM: human

<400> SEQUENCE: 13
gtcagagaag ccatattt                         18

<210> SEQ ID NO 14
<211> LENGTH: 19
<212> TYPE: DNA
<213> ORGANISM: human

<400> SEQUENCE: 14
ttacactaag gaaaggggg                        19

<210> SEQ ID NO 15
<211> LENGTH: 20
<212> TYPE: DNA
<213> ORGANISM: human

<400> SEQUENCE: 15
gatttcttgg gatgtgcggg                       20

<210> SEQ ID NO 16
<211> LENGTH: 23
<212> TYPE: DNA
<213> ORGANISM: human

<400> SEQUENCE: 16
cactcagttt caagaaaaaa gtc                   23

<210> SEQ ID NO 17
<211> LENGTH: 20
<212> TYPE: DNA
<213> ORGANISM: human

<400> SEQUENCE: 17

```
gcttcttcaa gtcttcttcc                                          20

<210> SEQ ID NO 18
<211> LENGTH: 18
<212> TYPE: DNA
<213> ORGANISM: human

<400> SEQUENCE: 18
tgataagttg aagtctcg                                            18

<210> SEQ ID NO 19
<211> LENGTH: 19
<212> TYPE: DNA
<213> ORGANISM: human

<400> SEQUENCE: 19
atcttcatca tcttccacc                                           19

<210> SEQ ID NO 20
<211> LENGTH: 20
<212> TYPE: DNA
<213> ORGANISM: human

<400> SEQUENCE: 20
agttgaacga gtggttgggc                                          20

<210> SEQ ID NO 21
<211> LENGTH: 19
<212> TYPE: DNA
<213> ORGANISM: human

<400> SEQUENCE: 21
gaaagccata gccagttgc                                           19

<210> SEQ ID NO 22
<211> LENGTH: 20
<212> TYPE: DNA
<213> ORGANISM: human

<400> SEQUENCE: 22
ggtggacggc gaagtaaagc                                          20

<210> SEQ ID NO 23
<211> LENGTH: 20
<212> TYPE: DNA
<213> ORGANISM: human

<400> SEQUENCE: 23
agccctttgc tttccagagg                                          20

<210> SEQ ID NO 24
<211> LENGTH: 17
<212> TYPE: DNA
<213> ORGANISM: human

<400> SEQUENCE: 24
```

```
aacaatatgt ccttaca                                              17
```

<210> SEQ ID NO 25
<211> LENGTH: 17
<212> TYPE: DNA
<213> ORGANISM: human

<400> SEQUENCE: 25

```
aacaatatat ccttaca                                              17
```